United States Patent [19]
Müller et al.

[11] Patent Number: 5,804,384
[45] Date of Patent: Sep. 8, 1998

[54] DEVICES AND METHODS FOR DETECTING MULTIPLE ANALYTES IN SAMPLES

[75] Inventors: Uwe Richard Müller, Plano; David J. Lane, Wheaton, both of Ill.

[73] Assignee: Vysis, Inc., Downers Grove, Ill.

[21] Appl. No.: 761,131

[22] Filed: Dec. 6, 1996

[51] Int. Cl.⁶ .............. C12Q 1/68; C12M 1/00; G01N 33/566; C12N 15/00
[52] U.S. Cl. .............. 435/6; 435/7.1; 435/287.2; 435/287.3; 436/501; 436/514; 436/807; 536/23.1; 536/24.3; 530/350; 935/76; 935/77
[58] Field of Search .............. 435/6, 7.1, 283.1, 435/285.2, 286.5, 287.1, 287.2, 287.3, 187; 530/350; 536/23.1, 24.3, 25.3; 356/344; 422/50, 63, 68.1, 69, 98, 99; 436/501, 514, 807

[56] References Cited

U.S. PATENT DOCUMENTS

| | | | |
|---|---|---|---|
| 4,603,114 | 7/1986 | Hood et al. | 436/89 |
| 4,786,600 | 11/1988 | Kramer et al. | 435/235 |
| 4,960,691 | 10/1990 | Gordon et al. | 435/6 |
| 5,045,172 | 9/1991 | Guzman | 204/299 |
| 5,202,010 | 4/1993 | Guzman | 204/299 |
| 5,211,829 | 5/1993 | Imai et al. | 204/299 |
| 5,407,798 | 4/1995 | Martinelli et al. | 435/6 |
| 5,447,837 | 9/1995 | Urnovitz | 435/5 |
| 5,486,452 | 1/1996 | Gordon et al. | 435/5 |
| 5,490,909 | 2/1996 | Wang et al. | 204/452 |
| 5,534,123 | 7/1996 | Bashkin et al. | 204/455 |
| 5,582,801 | 12/1996 | DeWitt et al. | 422/131 |
| 5,584,982 | 12/1996 | Dovichi et al. | 204/603 |
| 5,587,128 | 12/1996 | Wilding et al. | 422/50 |
| 5,589,136 | 12/1996 | Northrup et al. | 422/102 |
| 5,653,939 | 8/1997 | Hollis et al. | 422/50 |

OTHER PUBLICATIONS

Schaffner et al., "Nanovariant RNAs: Nucleotide Sequence and Interaction with Bacteriophage Qβ Replicase", *J. Mol. Biol.* 117:877–907 (1977).

Tyagi et al., "Extremely Sensitive, Background–Free Gene Detection Using Binary Probes and Qβ Replicase", *Proc. Natl. Acad. Sci.* 93:5395–5400 (1996).

Zamora et al., "Design of Artificial Short–Chained RNA Species That Are Replicated Qβ Replicase", *Biochemistry* 34:1261–1266 (1995).

Beattie et al., "Advancex in Genosensor Research" *Clin. Chem.* 41:700–706 (1995).

Burg, et al., "Single Molecule Detection of RNA Reporter Probes By Amplification with Qβ Replicase", *Molecular and Cellular Probes* 10:257–271 (1996).

Fukami et al., "Template Specificity of Qβ and SP Phage RNA Replicase as Studied by Replication of Small Variant RNAs", *Molec. gen. Genet.*, 169:173–181 (1979).

Mills, et al., "Nucleotide Sequence of Microvariant RNA: Another Small Replicating Molecule", *Proc. Nat. Acad. Sci.* 72:4252–4256, (1975).

*Primary Examiner*—Bradley L. Sisson
*Attorney, Agent, or Firm*—Norval B. Galloway

[57] ABSTRACT

The invention features devices that each consist of a tube containing a linear array of specific binding elements that each have capture probes specific for a target analyte linked thereto. The devices of the invention can be used in methods for detecting target analytes in samples.

30 Claims, 5 Drawing Sheets

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
( A ) LENGTH: 40 base pairs
( B ) TYPE: nucleic acid
( C ) STRANDEDNESS: single
( D ) TOPOLOGY: linear ( i i ) MOLECULE TYPE: Genomic DNA ( x i ) SEQUENCE DESCRIPTION: SEQ ID NO:1:

GCTCCAATGA GAACCTCACC TAGCATCTGA CTTTGAGCCT 40

( 2 ) INFORMATION FOR SEQ ID NO:2:

( i ) SEQUENCE CHARACTERISTICS:
( A ) LENGTH: 40 base pairs
( B ) TYPE: nucleic acid
( C ) STRANDEDNESS: single
( D ) TOPOLOGY: linear ( i i ) MOLECULE TYPE: Genomic DNA ( x i ) SEQUENCE DESCRIPTION: SEQ ID NO:2:

ACTCAGCCAC TGGATTTAAG TAGCATCTGA CTTTGAGCCT 40

( 2 ) INFORMATION FOR SEQ ID NO:3:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: Genomic DNA ( x i ) SEQUENCE DESCRIPTION: SEQ ID NO:3:

TGAGGTTC TCATTGGAGC 18

( 2 ) INFORMATION FOR SEQ ID NO:4:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: Genomic DNA ( x i ) SEQUENCE DESCRIPTION: SEQ ID NO:4:

TAAATCCA GTGGCTGAGT                                                                        18

( 2 ) INFORMATION FOR SEQ ID NO:5:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( i i ) MOLECULE TYPE: Genomic DNA ( x i ) SEQUENCE DESCRIPTION: SEQ ID NO:5:

TAAATGCA GTGCCTGAGT                                                                        18

( 2 ) INFORMATION FOR SEQ ID NO:6:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( i i ) MOLECULE TYPE: Genomic DNA ( x i ) SEQUENCE DESCRIPTION: SEQ ID NO:6:

TATATGCA GTGCCTCAGT                                                                        18

( 2 ) INFORMATION FOR SEQ ID NO:7:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: Genomic DNA ( x i ) SEQUENCE DESCRIPTION: SEQ ID NO:7:

AGGCTCAA AGTCAGATGC TA                                                                     20

DEVICES AND METHODS FOR DETECTING MULTIPLE ANALYTES IN SAMPLES

STATEMENT AS TO FEDERALLY SPONSORED RESEARCH

This invention was supported in part by the U.S. Government under Advanced Technology Program project number 95-08-0012 and cooperative agreement number 70NANB5H1108, awarded by the Department of Commerce, and administered by the National Institute of Standards and Technology. The Government has certain rights in the invention.

BACKGROUND OF THE INVENTION

This invention relates to devices and methods for detecting multiple analytes in samples.

Detection of analytes present in trace amounts in a sample requires sensitive and specific methods. Otherwise, detection of such analytes may be hindered by the presence of substances found at higher concentrations in the sample. This problem is compounded if the analyte does not have a physical or chemical property that renders it easy to detect.

Genosensors are devices that include groups or sets of probes that facilitate detection of target nucleic acids in samples. For example, Beattie et al. (Clin. Chem. 41(5) :700–706, 1995) describes a flowthrough genosensor consisting of a single layer silicon wafer containing a 3×3 matrix of nucleic acid probes. A sample suspected of containing a target nucleic acid to which the probes can bind is passed through the genosensor by application of a slight vacuum or suction.

Another device used to detect target molecules in samples is a dipstick, which is an elongated strip containing a probe, such as an antibody. The dipstick is immersed into a sample suspected of containing a molecule that binds to the probe. For example, Urnovitz, U.S. Pat. No. 5,447,837 (1995), describes a dipstick that contains discrete areas, each containing different antibodies or antigens, for use in detecting the presence of corresponding antigens or antibodies in a sample.

SUMMARY OF THE INVENTION

The invention provides assay devices that each include a vessel or a channel (e.g., a tube) containing a linear array of binding elements, each having a binding factor, or probe, specific for a distinct target analyte linked thereto. The devices can be used in methods for the simultaneous analysis of multiple analytes in a sample. When used in these methods, a linear array of signals that resembles a barcode is generated in the devices.

Accordingly, in one aspect, the invention features an assay device for isolating an analyte (e.g., a nucleic acid, a polypeptide, a carbohydrate, a lipid, a metabolite, or a drug) from a sample. The assay device consists of a tube, such as a capillary tube, containing a linear array of binding elements that each are linked to a distinct binding factor, to which a corresponding specific component binds. Each of the binding elements in the assay device are configured to sealingly contact the interior surface of the tube along the entire circumference of the binding element. The binding elements can be configured to be adjacent to one another or they can be separated by regions lacking distinct binding factors.

The distinct binding factor of at least one of the binding elements can consist of a capture probe, in which case the corresponding specific component is a target analyte. Alternatively, the distinct binding factor of at least one of the binding elements can consist of a member of a specific binding pair, in which case the corresponding specific component is the other member of the specific binding pair and a capture probe that binds to the analyte.

The distinct binding factor of at least one of the binding elements can consist of a nucleic acid, for example, a nucleic acid that consists of a portion of an autocatalytically replicable nucleic acid, or a polypeptide.

In a second aspect, the invention features a method for detecting the presence of an analyte (e.g., a nucleic acid, a polypeptide, a carbohydrate, a lipid, a metabolite, or a drug) in a sample. In this method, the analyte is labeled with a detectable label (e.g., a detectable label that is provided by a detector probe, which can be, e.g., a nucleic acid or a polypeptide) and is contacted with a capture probe, which can be, e.g., a nucleic acid or a polypeptide, to form an analyte-capture probe complex on a specific binding element in a device of invention. Detectable label that is not specifically bound to the analyte in the complex is then removed from the device so that the detectable label on the binding element can then be detected as a measure of the presence of the analyte in the sample. Preferably, substantially all of the detectable label that is not specifically bound to the analyte in the complex is removed from the device. For example, preferably at least 50%, or, more preferably, at least 70%, 80%, 90%, 95%, or 100% of the unbound label is removed.

The distinct binding factor can consist of a capture probe and the contacting step can be carried out by passing the analyte through the device one or more times. The analyte can be passed through the device by, e.g., mechanical pumping or by application of an electric field to the analyte. The labeling step and the contacting step can be carried out simultaneously or, alternatively, the contacting step can be carried out before the labeling step.

In one example of the method of the invention, the analyte consists of a nucleic acid, the detector probe consists of a portion of an autocatalytically replicable nucleic acid on one end and a first analyte binding element on the other end, and the capture probe consists of the remainder of the autocatalytically replicable nucleic acid on one end and a second analyte-binding element on the other end. The first and second analyte-binding elements bind to adjacent nucleotide segments in the nucleic acid analyte. This method includes steps of (1) ligating the first and second analyte-binding elements to each other to form a replication template, and (2) replicating the template to generate the detectable signal.

Rather than being a capture probe, the distinct binding factor of the binding element can be a member of a specific binding pair, and a separate capture probe can contain the other member of the specific binding pair. The contacting step can be carried out, e.g., by passing the sample and the capture probe through the device.

The invention also includes an assay system including a means for providing active fluid transport in fluid communication with the assay device of the invention. Also included in the invention is an assay system including a fluid transporter that is in fluid communication with the device of the invention.

Also included in the invention is an assay device for isolating an analyte from a sample, which device includes a channel (e.g., a tube or a channel etched into a surface, such as a glass surface) having an interior lumenal surface and containing a linear array of binding elements. Each of the binding elements in this device includes a distinct binding factor, to which a corresponding specific component binds. In addition, each of the binding elements in this device includes the lumenal surface of a distinct region of the channel. At least one of the distinct binding factors in this device is bound to at least one of the binding elements by a method such as photolithography or chemical coupling (see below).

The invention provides several advantages, as it permits simultaneous analysis of multiple analytes in a sample on a micro-scale with high sensitivity. Because detected analytes are physically separated on the devices, it is not necessary to use distinct labels on detector probes that are specific for different analytes. The methods of the invention also require only small sample and reagent volumes (although large volumes can be used, if desired), and are rapid and readily adaptable to automation. A key feature of the devices is their capacity to isolate and concentrate an analyte from a dilute solution into a small capture zone (i.e., a binding element) in a device of the invention, which represents a physical amplification. This provides for increased sensitivity and avoids the need for enzymatic amplification, such as by use of the polymerase chain reaction (PCR), in some applications.

In certain embodiments, the probes used in the devices and methods of the invention are nucleic acids. A pair of nucleic acid molecules (or two regions within a single nucleic acid molecule) are said to "hybridize" to each other if they form a duplex by base pairing interactions between them. As is known in the art, hybridization between nucleic acid pairs does not require complete complementarity between the hybridizing regions, but only that there is a sufficient level of base pairing to maintain the duplex under the hybridization conditions used.

Hybridization reactions are typically carried out under "stringent conditions," e.g., low to moderate stringency conditions, in which specific and some non-specific interactions can occur. After hybridization, washing can be carried under higher stringency conditions to eliminate non-specific binding. As is known in this field, optimal washing conditions can be determined empirically, e.g., by gradually increasing the stringency. Condition parameters that can be changed to affect stringency include, e.g., temperature and salt concentration. In general, the lower the salt concentration and the higher the temperature, the higher the stringency. For example, washing can be initiated at a low temperature (e.g., room temperature), using a solution containing an equivalent or lower salt concentration as the hybridization solution. Subsequent washing can be carried out using progressively warmer solutions having the same salt solution. Alternatively, the salt concentration can be lowered and the temperature maintained in the washing step, or the salt concentration can be lowered and the temperature increased. Such standard variations are known in the art. Additional parameters can be altered to affect stringency including, e.g., the use of a destabilizing agent, such as formamide.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

As further described below (see Example II), an example of hybridization conditions that can be used in the methods of the invention involves hybridization at room temperature in 3×SSC, and subsequent washing in 3×SSC. Thus, in this example, the stringency is not varied from the hybridization to the wash. In another example described below (see Example II), hybridization is carried out at room temperature in 3×SSC, and subsequent washes are carried out in 3×SSC at the following temperatures: 25° C., 42° C., 52° C., 58° C., and 70° C.

Another example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10–15 minutes each, in the order listed above, repeating any or all of the steps listed. However, as mentioned above, optimal conditions will vary, depending on the particular hybridization reaction involved, and can be determined empirically.

Similar to nucleic acid hybridizations, protein-protein binding reactions and subsequent washing to eliminate non-specific binding, can be carried out under varying conditions, depending on the affinities of the proteins for each other. For example, a binding reaction can take place in a buffer having physiological salt concentrations, and washing can be carried out using buffers having increasing salt concentrations. The stringency of the washing conditions can also be increased by including detergents, such as TWEEN-20™, and TRITON-X™, in the wash solution.

The members of a pair of molecules (e.g., a detector probe or a capture probe and a target analyte, or the members of a specific binding pair (e.g., antibody-antigen, nucleic acid, and protein-vitamin binding pairs)) are said to "specifically bind" to each other if they bind to each other with greater affinity than to other, non-specific molecules. For example, an antibody raised against an antigen to which it binds more efficiently than to a non-specific antigen can be described as specifically binding to the antigen. Similarly, a nucleic acid probe can be described as specifically binding to a nucleic acid target if it forms a specific duplex with the target by base pairing interactions.

Unless otherwise defined, all technical and scientific terms used herein have the same meaning as commonly understood by those of ordinary skill in the art to which this invention belongs. Although methods and materials similar or equivalent to those described herein can be used in the practice or testing of the invention, some preferred methods and materials are described below. All publications, patent applications, patents, and other references mentioned herein are incorporated by reference in their entirety. In case of a conflict, the present specification will control. In addition, the described materials and methods are illustrative only and are not intended to be limiting.

Other features and advantages of the invention will be apparent from the following detailed description and the claims.

DETAILED DESCRIPTION

Figure 1:
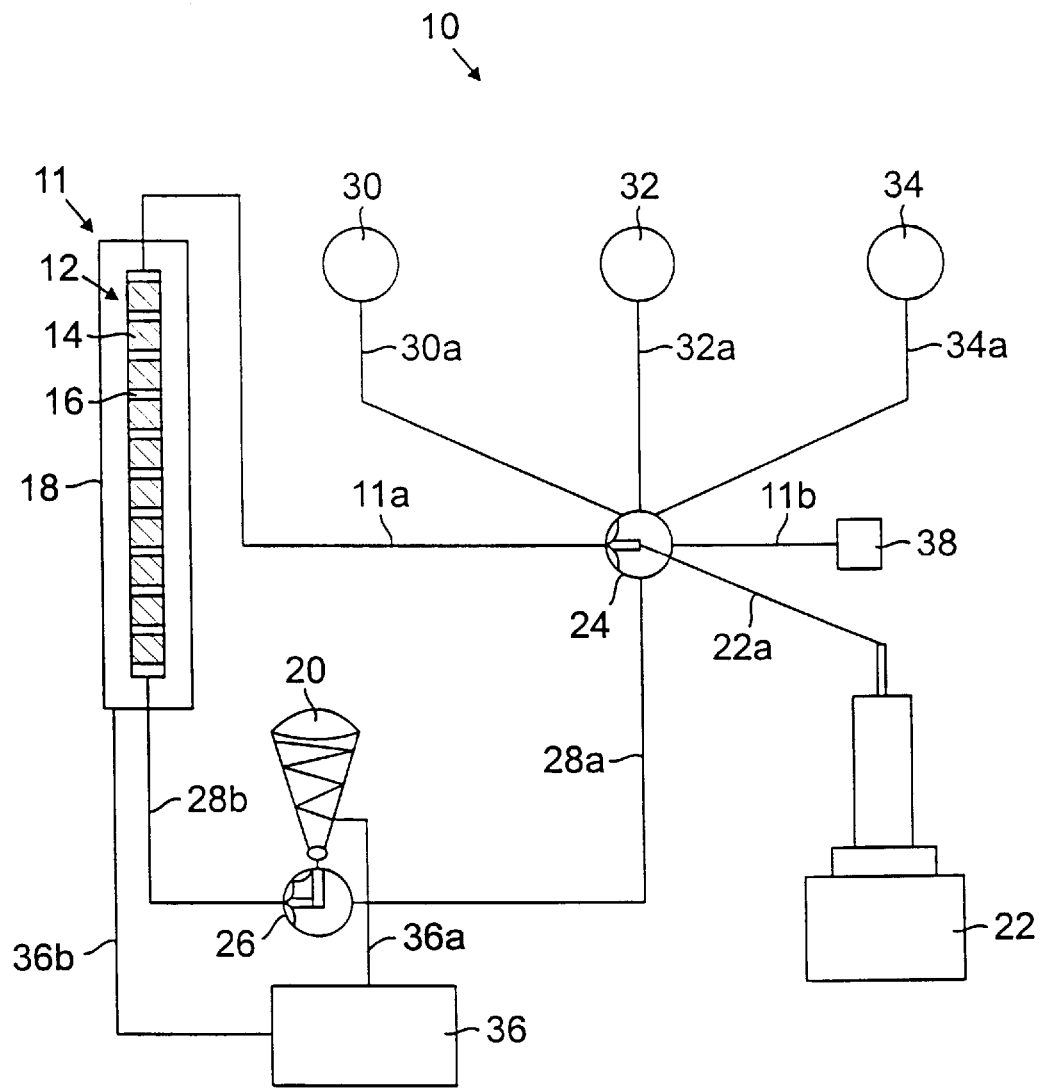
FIG. 1 is a schematic representation of an automated assay system for using a device of the invention.

The invention provides devices and methods for detecting multiple target analytes (e.g., up to 100 or more different analytes) in samples. A central feature of the methods of the invention is the specific binding of probes to target analytes. This can be carried out by using, e.g., a sandwich hybridization assay (see, e.g., Ranki et al., Gene 21:77–85, 1983; U.S. Pat. No. 4,486,539 (1984)). Sandwich hybridization assays involve the use of a capture. probe and a detector probe, which are designed to bind concurrently to a target analyte to form a capture probe-analyte-detector probe complex. In the context of the present invention, the detector probe contains a detectable label, and the capture probe either (1) contains the first member of a specific binding pair, or (2) is immobilized on a specific binding element of a device of the invention (see below). In either of these cases, the use of a capture probe facilitates purification of analyte-probe complexes from sample components, as well as from unbound detector probes.

In addition to sandwich hybridization assays, in which the detectable label is provided as part of a detector probe, assays in which the target itself is labeled can be used. In such assays, detector probes are not required. For example, before or after contact with a device of the invention, targets can be amplified by PCR in the presence of labeled nucleotides, e.g., fluorescently or isotopically labeled nucleotides. Similarly, targets can be labeled in primer extension reactions containing labeled nucleotides. Targets can also be labeled metabolically by, e.g., contacting cells producing the target with a labeled component (e.g., a nucleotide or amino acid) of the target. Labeled targets are immobilized on specific binding elements of a device of the invention by binding to a specific capture probe, as described above. Detector probes are also not required when detection of intercalating dyes (e.g., ethidium bromide or propidium iodide) is used to measure duplex formation between nucleic acid capture probes and analytes.

One example of a device included in the invention consists of a vessel or channel (e.g., a tube, such as a capillary tube) containing a linear array of binding elements, each containing, as a binding factor on the binding element, an immobilized, distinct capture probe specific for a corresponding analyte. This device can be used in several methods in which capture probe-analyte-detector probe complexes are formed on the binding elements. Preferably, the analyte and detector probe are contacted with each other to form an analyte-detector probe complex prior to their contact with the capture probe. The binding elements of the device can then be contacted with a sample containing the analyte-detector probe complex by, e.g., mechanical or electrophoretic transport of the sample through the device. A capture probe-analyte-detector probe complex is formed as the analyte-detector probe complex contacts its corresponding binding element in the device.

In a variation of this method, a sample containing an analyte is applied to a device of the invention so that a capture probe-analyte complex is formed on a binding element of the device, before the analyte is contacted with a detector probe. A detector probe that specifically binds to the analyte and contains a detectable label is then contacted with the capture probe-analyte complex formed on the binding element. In another variation of this method, the sample containing the analyte and the detector probe are individually contacted with the device at the same time.

If desired, samples and probes can be passed through the device multiple times, to increase the likelihood of specific binding between a capture probe and its corresponding analyte or analyte-detector probe complex. If such a method is used, the order of contact between the capture probe, analyte, and detector probe is less pertinent. Multiple passages of samples and probes through the device can be facilitated by, for example, the use of tubing that is connected to both ends of the device. The sample and probes can be pumped repeatedly through the device and tubing using a peristaltic pump. In the case where the sample and probe are passed through the device only once, it is preferable to form detector probe-analyte complexes before these components are contacted with the device.

Unbound detector probes and non-specifically bound sample components can be removed from the device by the use of, e.g., an active fluid transporter, such as a mechanical pump (e.g., a piezoelectric pumping device), that is configured to be in fluid communication with the assay device, electrophoresis, application of a vacuum, or a combination of these methods, depending on the compositions of the device and the bound complexes. Detection of labels on the binding elements of the device corresponding to the specific capture probes can be used as a measure of the presence of the corresponding analytes in the sample.

A second example of a device included in the invention consists of a channel (e.g., a tube) containing a linear array of binding elements, each binding element having linked (e.g., by a covalent or non-covalent linkage) thereto, as a binding factor, an immobilized member of a particular specific binding pair. This device can be used in a method in which the binding elements of the device are contacted with a sample, capture probes (each of which contains the other member of a particular specific binding pair), and labeled detector probes by, e.g., mechanical or electrophoretic transport of the sample and the probes through the device. If desired, to increase the likelihood of specific complex formation, the sample and the probes can be passed through the device multiple times. Unbound detector probes and non-specifically bound sample components can then be washed from the device by, e.g., the use of a fluid transporter, such as a mechanical pump (e.g., a piezoelectric pumping device), electrophoresis, application of a vacuum, or by a combination of these methods, depending on the compositions of the device and the bound complexes. Detection of labels on the binding elements of the device corresponding to the particular specific binding pairs can be used as a measure of the presence of the analytes in the sample. The sample, the detector probes, the capture probes, and the device can be contacted with one another in any order in this method of the invention. Preferably, the capture probe-analyte-detector probe complex is formed prior to introducing the sample into the device.

An advantage of this particular device, containing a linear array of binding elements, each of which contains a distinct set of members of particular specific binding pairs, is that a single device can be used to detect virtually an infinite number of analytes. The only elements in this system that need to be changed to accomplish this are the analyte-binding regions of the capture and detector probes. In cases where the levels of intercalating dye on the binding elements are measured (see above), the only component of this system that needs to be changed for each analyte is the analyte-specific binding region of the capture probe.

Devices

The devices of the invention consist of a channel, such as a tube, containing a linear array of binding elements, each having linked thereto either (1) an analyte-specific capture probe, or (2) a member of a particular specific binding pair. As described below, the devices of the invention can embody a number of formats.

For example, FIG. 1 shows an automated assay system 10 including a device 11 of the invention. Device 11 includes a linear array 12 of binding elements 14 layered in a one-dimensional stack in the lumen of a tube, such as a capillary tube 18. The binding elements in this format can consist of any standard column-packing material. For example, glass microbeads, fritted glass, sintered glass, silicon, agarose beads, glass wool, or a gel, such as a polyacrylamide gel, can be used. Thus, binding elements can be made up of multiple, discrete subunits, such as beads, that are each linked to the same binding factor. It is the group of such similar subunits, each being linked to the same binding factor, that is the "binding element," rather than the individual subunits themselves. Devices containing such binding elements can be made using standard methods. For example, a plug can be placed in one end of a tube and the material of which a binding element is to be made can be placed in the other end of the tube. The binding element can then be positioned by applying suction to the end of the tube containing the plug. Additional binding elements can be added to the device by repeating this process, using the desired binding element material. The binding elements can be stacked directly on top of one another, or inert layers, lacking capture probes (or members of particular specific binding pairs), can be placed between them. The binding elements in such a stack should be configured and arranged so that they each sealingly contact the interior surface of the tube, i.e., so that they each contact the interior surface of the tube along their entire circumference. For example, if the tube has a circular cross-section, the binding elements would each also have a circular cross-section and a diameter slightly smaller than the internal diameter of the tube so that they can be press-fit into the tube. This configuration forces the fluid containing the analyte to flow through, rather than around, each of the binding elements in the stack.

The binding elements can also consist of stacks of filters or membranes, e.g., nylon or nitrocellulose membranes, to which the capture probes (or members of particular specific binding pairs) are immobilized. For example, a device can be made by covalently binding DNA probes to a nylon filter, then stacking multiple filters, containing multiple distinct probes, by placing a porous, inert, double-sided adhesive sheet between each filter.

The binding elements of the devices of the invention can be, e.g., 0.05 to 1 mm thick and have diameters of similar size. Binding elements having such dimensions can consist of, e.g., layers of polystyrene or glass beads, or, in the case of channels etched into a planar surface, such as a glass surface (see below), the binding elements can consist of a linear array of individual beads. Alternatively, the inside wall of etched channels of about 0.05 mm diameter, or the inside walls of capillary tubes having a similar diameter, can be activated by a laser to generate binding elements that are 0.02 mm to 1 mm thick (see below).

The binding elements are preferably designed to have surface to volume ratios that favor having all target analytes (or capture probe containing a member of a particular specific binding pair) pass through the device in close proximity to its corresponding capture probe (or the corresponding member of the particular specific binding pair). Selection of binding elements that have favorable surface area to volume ratios is readily within the grasp of one skilled in the art. For example, one may select a material that the sample and probes will flow around, such as glass or agarose beads, or, preferably, a material that the sample and probes will flow through, such as porous beads or filters. In either case, as is understood in the art, in addition to surface area to volume ratios, factors such as the potential flow rate through a material can be considered in selecting a material for use as a binding element.

The binding elements in a stack can be distinguished from one another by the capture probes (or the members of particular specific binding pairs) they contain, the materials of which they are made, and/or the presence of inert spacers (i.e., without capture probes) between them. Appropriate positive and negative controls can also be included in the stacks of binding elements of the device.

In addition to being linked to the filters, membranes, or other matrices described above, the capture probes (or the members of particular specific binding pairs) can be linked to distinct binding element regions on the lumenal wall of a channel, e.g., a tube, such as a capillary tube. Attachment of probes, such as nucleic acid and polypeptide probes, to such a surface can be carried out using any of a number of standard methods, including direct adsorption or chemical coupling to reactive groups on the surface. For example, a linker can be used, e.g., a flexible carbon chain, such as a 3-glycidoxypropyltri-methoxysilane linker (see, e.g., Maskos et al., Nucl. Acids Res. 20(7):1679–1684, 1992). Photolithography can also be used to make this type of device. In this method, the lumenal surface of a tube is coated with a photosensitive linker and a laser beam is directed at a region in the tube where the binding of a specific capture probe is desired. The probe is then passed through the tube where it binds to the laser-activated region. After washing away excess probe, another region of the tube is laser-activated and contacted with a different probe, and this process can be repeated until the desired number of binding elements are obtained (see, e.g., U.S. Pat. No. 5,143,854; WO 92/10092; and WO 90/15070). Similar methods can be used to make devices in which the binding elements consist of capture probes linked to regions of the lumenal wall of a channel etched into a planar surface, such as a glass plate.

The new devices can be included in an automated assay system. For example, an automated assay system 10 including an assay device 11 is schematically illustrated in FIG. 1. A linear array 12 of binding elements 14, each separated by inert spacers 16, in this device 11 is contained within a capillary tube 18. A sample suspected of containing a target analyte is introduced into a mixing chamber 20 and then is moved from the mixing chamber 20 into the device 11 by an automated system 10, including a syringe pump 22, two valves 24 and 26, and fluid lines 11a, 11b, 22a, 28a, 28b, 30a, 32a, and 34a. The system also includes reservoirs containing hybridization buffer 30, wash buffer 32, and one or more detector probes 34. Mechanical operation of the system, e.g., the opening and closing of the valves 24 and 26, can be controlled by a computer (not shown). The steps for detecting a nucleic acid analyte in a sample using this assay system 10 are described briefly as follows.

Hybridization buffer is drawn from the hybridization buffer reservoir 30 through fluid line 30a, valve 24, fluid line 22a, and into the syringe pump 22, and then is pumped through fluid line 22a, valve 24, fluid line 28a, and valve 26 into the mixing chamber 20, which contains a sample suspected of containing a target analyte. Detector probe is then withdrawn from the detector probe reservoir 34 and is pumped through fluid line 34a, valve 24, fluid line 28a, and valve 26 into the mixing chamber 20, where it is mixed with the sample by rapid pulsation by the syringe pump 22. The sample-probe mixture is then heated in the mixing chamber 20 by a heater 36 via conduit 36a to a temperature that facilitates hybridization of target analytes to detector probes. The mixture is then drawn back into the syringe pump 22 via valve 26, fluid line 28a, valve 24, and fluid line 22a and is then pushed via fluid line 22a, valve 24, and fluid line 11a through the device 11, which has been preheated by the heater 36 via conduit 36b, and then back into the mixing chamber 20 via fluid line 28b. During this step, the mixture passes through the linear array of binding elements 12 in the device 11.

Any target-detector probe complex that contacts a probe on a binding element 14 in the linear array 12 of binding elements 14 that has a sequence complementary to a target analyte sequence is immobilized on the binding element 14. This process can be repeated several times, until a sufficient percentage of the target analytes have been captured on a binding element 14 in the linear array 12 of binding elements 14.

The mixture is then pumped via fluid line 28b, valve 26, fluid line 28a, valve 24, and fluid line 11b to a waste collection chamber 38, and wash buffer is drawn from the wash buffer reservoir 32 via fluid line 32a, valve 24, and fluid line 22a into the syringe pump 22 and is then pushed via fluid line 22a, valve 24, and fluid line 11a through the device 11 to remove all unbound material, such as unbound detector probes, from the device 11. Wash buffer is pumped via fluid line 28b, valve 26, fluid line 28a, valve 24, and fluid line 11b to the waste collection chamber 38 after each cycle and several wash cycles can be carried out to reduce non-specific binding. The assay device 11 can then be illuminated and scanned by an imaging system (see below).

Figure 2A:
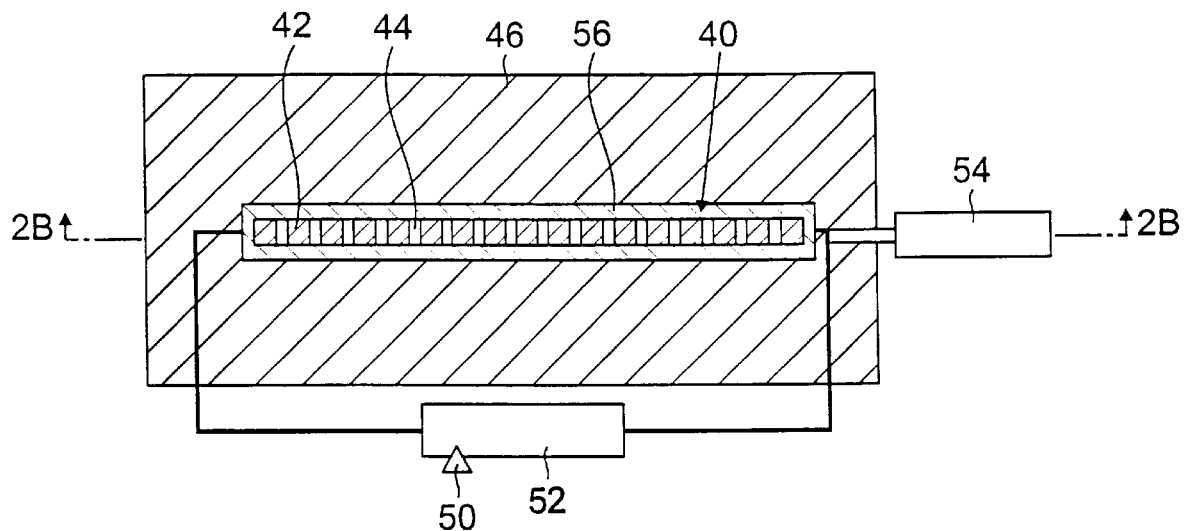
FIGS. 2A and 2B are schematic representations of a top view and a side, cross-sectional view along line 2B—2B in FIG. 2A, respectively, of an assay system for using another device of the invention.
Figure 2B:
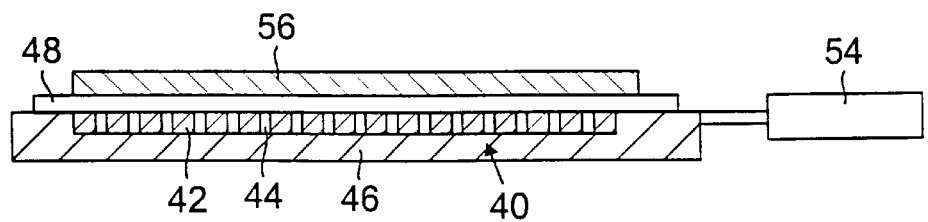

An example of an assay system including a device in which the binding elements consist of capture probes linked to regions of the lumenal wall of a channel etched into a planar surface is schematically illustrated in FIG. 2A (top view) and FIG. 2B (side, cross-sectional view). In this system, the linear array 40 of binding elements 42, each separated by inert spacers 44, is etched into the surface of a glass slide 46 that is covered by a glass coverslip 48. Mixtures containing detector probes and samples suspected of containing target analytes are introduced into the assay system by injection through the sample injection port 50. A pump 52 is used to push the mixture through the linear array 40 of binding elements 42. Detection of target-detector probe complexes bound to the binding elements 42 in the linear array 40 can be carried out using a laser 54 and a charge-coupled device (CCD) 56, which is placed on top of the glass coverslip 48 (see below).

Target Analytes

Target analytes that can be detected using the methods of the invention include a wide variety of molecules, e.g., nucleic acids, proteins, carbohydrates, lipids, metabolites, vitamins, and drugs. Detection of such molecules can be useful in fields such as medicine, forensics, agriculture, industry, food sciences, and veterinary medicine. For example, in the field of medicine, the methods of the invention can be used in the diagnosis of conditions (e.g., cancer) characterized by the presence or absence of specific markers (e.g., protein or nucleic acid markers) and/or altered levels of normally occurring proteins (e.g., hormones, cytokines, lymphokines, antibodies, or enzymes) or nucleic acids. The methods of the invention can also be used to detect gene mutations, which can be characterized by, e.g., single base pair changes, small or large deletions, insertions, or rearrangements (e.g., chromosomal translocations), and genetic polymorphisms. In addition, the methods of the invention can be used to detect the presence of an infectious pathogen (e.g., a bacterium, a virus, a protozoan, a parasite, or a fungus) or a rare cell (e.g., a fetal cell in maternal blood) in a sample, e.g., a sample from a patient.

In addition to binding distinct analytes, different binding elements in a linear array of a device of the invention can be designed to bind to different regions of a single analyte molecule. A device containing such a linear array can be used, e.g., to detect sequence variations in a nucleic acid. For example, sequence variations between different groups of organisms can be detected using this type of device. In this device, the collection of binding elements is selected so that one or more patterns of binding correspond collectively to a sequence variation found in a particular group of organisms, and other patterns correspond to other groups of organisms. For example, probes targeting various portions of rRNA molecules can be used in sets (e.g., 6 or 7 sets) to fully include the greater than 2,000 known Salmonella strains. As another example, *Shigella flexneri* and *Escherichia coli* rRNAs are so closely related that use of a single probe would not likely distinguish all Shigella from all *E. coli*, but a panel of 7 or 8 probes collectively could be used to distinguish these organisms.

Samples that can be tested using the methods of the invention include, e.g., biological fluids, such as blood, serum, plasma, urine, and saliva, as well as plant extracts, cell or tissue extracts, cell culture media, environmental samples, and fermentation mixtures. If necessary, protein and/or nucleic acid preparations can be extracted from the samples using standard methods, before the present method is applied. Due to the sensitivity of the methods of the invention, only small amounts of samples are required.

Probes

The types of specific probes used in the methods of the invention depend on the particular type of target analyte to be detected, and are well known in the art. For example, in the case of a nucleic acid target (e.g., a DNA or an RNA target), nucleic acid probes can be used. The nucleic acid probes can contain deoxyribonucleotides, ribonucleotides, or combinations or modifications thereof. The optimal sequences, lengths, and levels of complementarity with the target analyte, to achieve specific binding, are parameters that are readily determined by those skilled in the art. For example, the probes can contain at least 8, preferably 16–100, or most preferably 18–40, consecutive nucleotides that are complementary to the target nucleic acid analyte. The design of such probes can be facilitated by reference to standard protocol manuals and publicly available computer programs (see, e.g., Ausubel et al., eds. *Current Protocols in Molecular Biology*, Wiley & Sons, New York, 1989). Synthesis of nucleic acid probes can be carried out using standard chemical or recombinant methods. Alternatively, nucleic acid probes can be purchased from commercial vendors. In addition to nucleic acid probes, nucleic acid target analytes can be detected using other probes, such as polypeptide probes, e.g., polypeptide probes that contain nucleotide sequence-specific nucleic acid binding domains.

In the case of protein targets (e.g., antibodies, hormones, enzymes, pathogen proteins, cytokines, and lymphokines), antibodies, such as monoclonal antibodies that specifically bind to an analyte, can be used in the methods of the invention. Techniques for producing antibodies are well known in the art (see, e.g., Harlow et al., *Antibodies, A Laboratory Manual*, Cold Spring Harbor Laboratory Press, Cold Spring Harbor, New York, 1988). Particularly useful antibody molecules include Fab fragments of immunoglobulins, as well as recombinantly made single chain antibodies (see, e.g., Huston et al., U.S. Pat. Nos. 5,091,513 (1992) and 5,132,405 (1992); and Ladner et al., U.S. Pat. Nos. 4,704,692 (1987) and 4,946,778 (1990)). In addition to antibodies, non-antibody proteins, nucleic acids, and other molecules that specifically bind to target protein analytes can be used.

The detector probes can be labeled with, e.g., fluorescent labels (e.g., fluorescein, rhodamine, or Texas Red), enzyme labels (e.g., alkaline phosphatase, glucose oxidase, horseradish peroxidase, urease, luciferase, or galactosidase), chromophores, phosphorescent agents, luminescent agents, radioactive labels, colored labels, or combinations thereof. An advantage of the present invention is that, due to the physical separation of the different specific detector probes on the device, a single label can be used on multiple, distinct detector probes in the same assay.

Although the use of a detector probe increases the specificity of the assay, as is mentioned above, detector probes are not required for all of the methods included in the invention. For example, detector probes are not required in cases where the target itself is labeled (e.g., by PCR, primer extension, or metabolic labeling), either before or after contact with a capture probe. Detector probes are also not required when capture probe-analyte binding is monitored by detection of the levels of an intercalating dye, such as ethidium bromide or propidium iodide, captured on a binding element by duplex formation between a nucleic acid capture probe and analyte. Similarly, detector probes that do not contain labels can be used when detector probe-analyte binding is monitored by detection of the levels of an intercalating dye captured on a binding element by duplex formation between a nucleic acid detector probe and an analyte.

As mentioned above, capture probes used in the method of the invention can, e.g., (1) contain a member of a specific binding pair, or (2) be immobilized on a specific binding element of a device of the invention. Binding pairs can be used to direct specific target analytes to their correct, predetermined binding elements, rather than direct attachment of capture probes to binding elements. For example, a capture probe for a specific target analyte can contain one member of a specific binding pair, and the other member of the binding pair can be attached to a particular binding element in the linear array. Upon contacting the sample with the linear array, the target analytes are specifically localized to particular binding elements by the mutual recognition of the two members of the binding pair for each other. Binding pairs that can be used with capture probes include, e.g., vitamin-vitamin binding proteins (e.g., avidin-biotin and streptavidin-biotin), as well as antibody-hapten (e.g., digoxigenin-anti-digoxigenin, FITC (fluorescein-isothiocyanate)-anti-FITC, and any other hapten-anti-hapten antibody, many of which are commercially available), enzyme-substrate, enzyme-enzyme binding protein (e.g., $\beta$-galactosidase and APTG (para-amino-phenyl-$\beta$-D-thiogalactopyranoside), receptor-ligand (or antagonist) (e.g., a hormone binding to a hormone receptor, e.g., hIL-1ra binds to human interleukin receptor-like interleukin-1), nucleic acid-nucleic acid binding protein, nucleic acid-nucleic acid binding pairs, and other specific binding pairs known in the art. The other member of the specific binding pair, or the capture probe itself, can be immobilized on a binding element of the device using standard methods. For example, probes can be attached to a surface (e.g., a smooth or porous surface made of, e.g., glass, plastic (e.g., polypropylene), silicon, gold, or platinum) by the use of a linker, e.g., an epoxysilane linker, such as a 3-glycidoxypropyltri-methoxysilane linker (see, e.g., Maskos et al., supra; Beattie et al., supra). Photolithography may also be used (see above).

An example of a specific binding pair that can be used in the invention is a pair of complementary oligonucleotides. Optimal lengths, sequences, and levels of complementarity of oligonucleotides for use as specific binding pairs can be readily determined by one skilled in the art, and can vary depending on factors including sequence composition, sample complexity, and assay conditions (e.g., ionic strength, types of salts used, the presence of organic solvents, and/or hybridization temperature). For example, a nucleic acid containing alternating repeats, such as (AGTC)n (where n=the number of repeats) can be used as a member of a specific binding pair, and its complement, containing alternating repeats of (GACT)n, can be used as the other member of the binding pair. In addition to nucleic acids containing repeated sequences, pairs of nucleic acids containing complementary random sequences can be used as binding pairs in the invention. For example, pairs of nucleic acids, each containing, for example, at least 16 nucleotides (e.g., at least 20 nucleotides) can be used. Such random sequences, which statistically would be unique in the human genome, provide greater specificity. It is possible that shorter sequences may find complementary non-target sequences in analyte mixtures of high complexity. Pairs of homopolymeric oligonucleotides (e.g., poly-A/poly-T and poly-G/poly-C) can also be used as binding pairs in the invention.

Enzymatic Amplification of Detector Probes

In addition to detector probes having detectable labels attached to them, such as the probes described above, the methods of the invention can employ detector probes that contain all or a portion of a nucleic acid that can be enzymatically amplified to generate a detectable signal. For example, a detector probe containing all or a portion of a nucleic acid, such as midi-variant-1 (MDV-1) RNA, that is autocatalytically replicable in the presence of an enzyme, such as Q$\beta$ replicase, can be used.

Autocatalytically replicable nucleic acids, and corresponding enzymes that replicate them, are well known in the art and can be readily adapted for use in the methods of the invention. For example, MDV-1 RNA, nano-variant RNA, mini-variant RNA, and micro-variant RNA, which all are replicable by Q$\beta$ replicase, can be used (see, e.g., Kramer et al., U.S. Pat. No. 4,786,600; Burg et al., Molecular and Cellular Probes 10:257–271, 1996; Munishkin et al., J. Molecular Biology 221:463–472, 1991; Mills et al., Proc. Natl. Acad. Sci. USA 72(11):4252–4256, 1975; Schaffner et al., J. Mol. Biol. 117:877–907, 1977; Zamora et al., Biochemistry 34:1261–1266, 1995).

In addition to nucleic acids replicable by Q-beta replicase, other nucleic acids, such as nucleic acids derived from bacteriophage RNA genomes, that are replicable by other RNA-dependent RNA polymerases, can be used in the invention. For example, nucleic acids derived from SP phage (Fukami et al., Molec. Gen. Genet. 169:173–181, 1979), MS2, R17, and F2 (Inokuchi et al., Virology 96:323–326, 1979; Inokuchi et al., J. Mol. Biol. 158:711–730, 1982). Nucleic acids derived from brome mosaic virus RNA can also be used (Quadt et al., Proc. Natl. Acad. Sci. USA 90:1498–1502, 1993).

A detector probe that contains the entire sequence of an autocatalytically replicable nucleic acid, such as MDV-1, with an analyte-specific probe segment placed at either end of the replicable sequence or embedded within it, can be used in the methods of the invention. Removal of non-specifically bound probes from binding elements is particularly important in methods employing this type of probe, as a non-specifically bound probe can be amplified to generate a signal as readily as a specifically bound probe. Thus, the use of this type of probe can lead to the generation of background signals or, alternatively, require additional measures (assay steps) to reduce background to acceptable levels.

Figure 3:
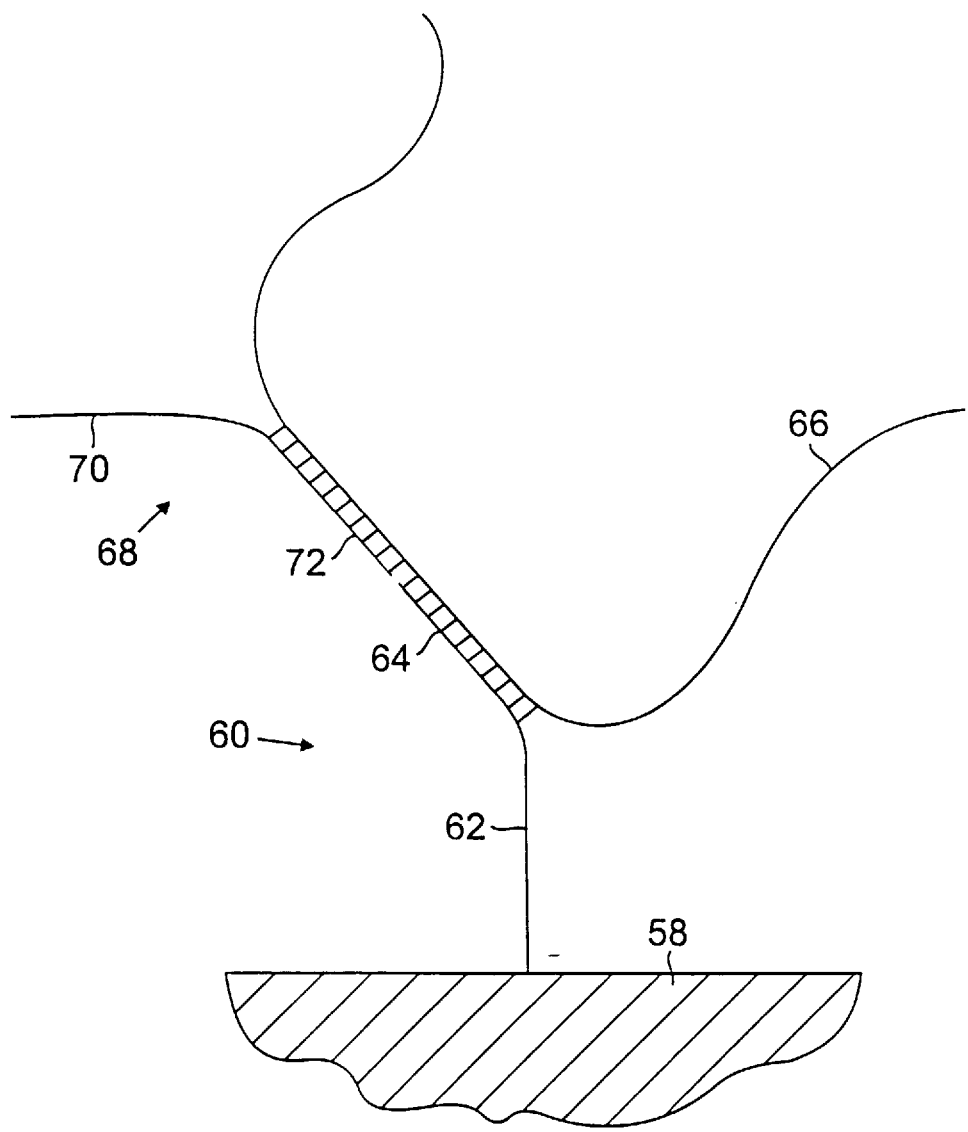
FIG. 3 is a schematic representation of a binding element having a capture probe linked thereto.

Binary probe pairs, consisting of two nucleic acid molecules, which together encompass the entire sequence of an enzymatically replicable nucleic acid, can be used to avoid the potential background problems associated with the replicable probes described above (see, e.g., Tyagi et al., Proc. Natl. Acad. Sci. USA 93:5395–5400, 1996; Martinelli et al., U.S. Pat. No. 5,407,798). The use of binary probe pairs is schematically illustrated in FIG. 3. In this example, a detector probe 68 contains a 3' portion of an autocatalytically replicable nucleic acid 70 at its 3' end and an analyte-specific probe 72 at its 5' end. The capture probe 60, which, in this example, is linked to the binding element 58 (the capture probe can also contain a member of a specific binding pair, see above), contains the 5' portion of the autocatalytically replicable nucleic acid 62, with an analyte-specific probe 64 at its 3' end. The probes can be designed so that, when bound to an analyte 66, the 3' end of the 5' probe 68 is adjacent to the 5' end of the 3' probe 60. The bound 5' probe 68 and 3' probe 60 can be ligated (i.e., covalently joined) together to generate a template for auto-catalytic replication. The use of such binary probes decreases the possibility of signal generation in the absence of specific binding between the capture probe, the analyte, and the detector probe, as covalent joining of the capture and detector probes is required to generate the autocatalytically replicable template.

The detector and capture probes used in such binary probe pairs can both be made of DNA, both be made of RNA, or one of the probes can be made of DNA and the other probe made of RNA. Additionally, either or both probes can be of mixed DNA/RNA composition. The probes can be made, e.g., using standard molecular methods or by standard phosphoramidite chemistry. The use of 5' and 3' portion probes that are both made of RNA can result in the generation of background signals, as such probes can promote RNA recombination reactions in the presence of Qβ replicase, resulting in the production of a replicable RNA template, in the absence of analyte-dependent ligation. The use of a 5' portion probe made of DNA and a 3' portion probe made of RNA in such a binary probe system provides a major advantage, as it suppresses such RNA recombination reactions. As a consequence, much higher levels of unligated, free probes can be present during the Qβ amplification reaction, substantially decreasing the assay requirements for removal of unhybridized probes. In addition, the use of a DNA 5' fragment with an RNA 3' fragment allows the chimeric ligation product to replicate with similar efficiency as an all-RNA template, which is replicated significantly more efficiently than an all-DNA template. A general example of such a chimeric, binary probe is described as follows.

A 5' probe can consist of a DNA version of a portion of MDV-1 (or another autocatalytically replicable template), joined with a probe element complementary to a portion of an analyte nucleic acid at its 3' end. A 3' probe can consist of an RNA containing a probe sequence that is complementary to the analyte region contiguous with that bound by the 5' probe at its 5' end, and the remainder of the replicable RNA sequence at its 3' end. The probe sequence elements of each of the probes can be separated from the replicable sequences by one or more spacer elements to improve the replicability of the joined DNA:RNA chimeric product.

The two probes are hybridized to a target nucleic acid and are ligated using, e.g., T4 DNA ligase, or any of a number of chemical reagents, e.g., cyanogen bromide, cyanoimidazole, 1-methyl cyanoimidazole, carbonyl diimidazole, or a water-soluble carbodiimide. The ligation product is contacted with an enzyme, such as Qβ replicase, and nucleoside triphosphates, to promote replication and generation of detectable amounts of a replication product. The replication product is detected by, e.g., staining with a dye that intercalates into the replication product (e.g., ethidium bromide or propidium iodide), or by hybridization with a probe that specifically binds to the replication product.

Capillary Electrophoresis

As mentioned above, binding of analytes and probes to the binding elements of the device can be facilitated by, e.g., electrophoretic and/or mechanical pumping of the sample and the probes through the device.

In the case of electrophoretic transfer, the linear array of binding elements of the device can be contained within an elongated channel, such as a capillary tube, which is made of glass, plastic, or other material, and has an internal diameter of, for example, less than about 1–2 millimeters, e.g., less than 500 microns. For example, a capillary tube having an internal diameter of 100 microns and a length of 50 millimeters can be used. Higher surface area to volume ratios can be achieved by using thinner capillaries, thereby facilitating more rapid hybridization kinetics. The use of a capillary tube having a high surface area to volume ratio, and thus a high capacity for dissipating heat, allows high voltages to be used, thus facilitating acceleration of the assays. In addition, the high surface area to volume ratio of capillary tubes facilitates target analyte hybridization to the probes, as any target molecule that passes through the capillary is in close proximity to the probes.

Another consequence of the high surface area to volume ratio of capillary tubes with respect to the present invention is that only very small quantities of reagents and analytes are required, the latter being in a small or large sample volume. For example, since only a few hundred fluorophores are needed for detection by a CCD device (see, e.g., Mackay et al., U.S. Pat. No. 4,874,492 (1989)), after fluorescence induction by a laser, a single milliliter of blood, which contains approximately $10^6$–$10^7$ white blood cells, will provide a sufficient amount of target for detection using the methods of the invention. In the case where bacterial rRNAs are the target analytes, a single bacterium in a one milliliter sample should be detectable using the methods of the invention.

Methods for carrying out capillary electrophoresis are well known in the art and are described, e.g., by Novotny et al. (Electrophoresis, 11:735–749, 1990). Any of several standard capillary electrophoresis systems can be used to carry out the method of the invention. For example, the Beckman P/ACE System 2050 (Beckman Instruments, Columbia, Md.) can be used. In addition, systems that facilitate simultaneous processing of several capillary tubes can be used (see, e.g., Yeung et al., U.S. Pat. No. 5,324,401 (1994)).

In addition to capillary electrophoresis, other electrophoretic methods can be used in the method of the invention. For example, electrophoresis can be carried out in a channel that has been etched into a plate, such as a glass or a plastic plate, and contains a linear array of binding elements. In this method, each end of the channel is in contact with a well into one of which the sample (and probes) is applied. This type of system allows analysis of larger sample volumes.

Detection of Labels Bound to Binding Elements

Emission, absorbance, or other detectable signal of the labels bound to the specific binding elements of the devices of the invention can be detected using any of several standard methods, depending on the nature of the label. For example, chromophore labels can be detected by measuring the absorbance of light at a specific wavelength with a spectrophotometer, while light generated by a chemiluminescent label can be detected using a luminometer or a CCD device. A CCD device can also be used to detect electromagnetic radiation of higher frequency (e.g., radiation from a radioisotopic label) or fluorescence generated from a fluorophore that has been excited at an appropriate wavelength with a standard mercury light source or a laser beam. To detect multiple target zones, the capillary can be scanned with a fiber optic device, or a CCD array can be placed adjacent to the capillary, but perpendicular to the excitation beam. The excitation beam can be part of the scanning device, for example, an inner fiber can carry the laser light, while surrounding fibers carry the fluorescent light back to the imaging system. In a different mode, the laser beam can be directed through one end of the capillary tube, either through the lumen, whereby the inside of the capillary acts as a light tunnel, or through the wall, which then acts as a wave guide. In the latter case, only fluorophore labels very close to the inside wall would get excited through a well known process called surface plasmon resonance. As will be apparent to those skilled in the art, appropriate filters, to remove scattered or reflected light, can be used with a detector device, such as a CCD device or a photomultiplier tube.

The detector can be positioned to specifically monitor the precise location in the device corresponding to a specific binding element and, if necessary, the linear array of binding pairs can be moved so that different specific binding elements are read by the detector. Alternatively, the detector can be moved along the device. In another example, involving the use of a capillary tube, neither the capillary containing the linear array of binding elements, nor the detector is moved. Rather, once complexes are formed on the binding elements, they are transported within the capillary tube so that they move past a detector. Such transport can be induced, e.g., by pumping fluid through the capillary to convectively move the linear array. In a device where the whole linear array is moved, whether contained in a capillary or not, the detector can be programmed to take a reading only at a predetermined time after the start of flow, such as the time determined to coincide with passage of the label. Also, a linear CCD device, spanning the length of the device, can be used. Appropriate systems integrating signal induction (e.g., lasers) and detection (e.g., CCD devices) devices are well known in the art (see, e.g., Fujimiya et al., U.S. Pat. No. 5,069,769 (1991); Pentoney, U.S. Pat. No. 5,208,466 (1993)).

To conduct a quantitative analysis of target analytes, a standard curve can first be prepared, using standard methods. For example, the amount of label detected using the method of the invention can be determined for several samples containing known quantities of the analytes. Standard curves generated by these readings can then be used to determine the concentrations of the analytes in a sample having unknown analyte concentrations, by comparing the levels of the signals detected to the standard curves.

EXAMPLES

Example I—Detection of Salmonella in a Biological Sample

The new methods and devices (e.g., the device illustrated in FIG. 1) can be used to detect the presence of pathogenic organisms in a sample, for example, for detection of Salmonella in a food sample. Reagents and methods adaptable for carrying out this assay are provided in the GENE-TRAK Salmonella Assay Kit (GENE-TRAK Industrial Diagnostics, Hopkinton, Mass.). Briefly, a device of the invention is made that includes a binding element having a poly-A probe linked thereto. A sample, a capture probe that is specific for a Salmonella nucleic acid and contains a poly-T tail, and a detector probe that is specific for the same Salmonella nucleic acid are then applied to an opening of this device.

If desired, the probes and sample can be transported through the device multiple times, e.g., by electrophoresis or by the use of a fluid transporter, such as a mechanical pump. After non-specifically bound material, such as unbound detector probe, is removed, the binding element of the device containing the poly-A probe is monitored for the presence of detector probe label, using a method appropriate for the type of label (e.g., see above).

In addition to Salmonella, the presence of other pathogens in the sample can be simultaneously monitored using the same device, provided the device contains binding elements containing, for each additional pathogen, (1) a probe specific for the other pathogen, or (2) a probe containing a member of a binding pair, the other member of which is a component of a probe specific for the other pathogen (note that the poly-A/poly-T binding pair used for detecting Salmonella could not be used to detect other pathogens in the same assay). Consistent with the description above, the probes for the other pathogens can be either attached directly to a binding element or can be capture probes that, in addition to binding to the pathogen-specific analyte, bind to a probe that is (1) bound to a binding element, and (2) distinct from the poly-A probe described above.

Example II—Detection of Chromosomal Translocations

The invention can be used to detect chromosomal translocations. As a specific example, the invention can be used to detect the so-called "Philadelphia" chromosome, the presence of which is frequently the underlying cause of acute lymphocytic leukemia (ALL) and chronic myelogenous leukemia (CML). The Philadelphia chromosome is characterized by having a balanced translocation of the terminal region of chromosome 9 to the terminal region of chromosome 22. This results in a gene fusion between the abl oncogene on chromosome 9 and the bcr gene on chromosome 22. This gene fusion is transcribed into a message containing regions corresponding to both genes.

The present invention can be used to detect such translocations as follows. A capture probe can be designed to hybridize to the bcr region of the fusion (either the gene itself or an RNA (pre-mRNA or mRNA) transcript thereof), while a detector probe can be designed to hybridize to the abl region. A device of the invention can be made in which the capture probe is linked to a specific binding element. Alternatively, a binding element of the device can contain a member of a specific binding pair (e.g., avidin) and the capture probe can contain the other member of the specific binding pair (e.g., biotin). In both cases, the sample, the capture probe, and the detector probe are contacted with the binding element, and upon removal of unbound components (e.g., unbound detector probe) by, e.g., electrophoresis or mechanical pumping, the presence of the abl detector probe on the bcr binding element is monitored. Capture of the abl detector probe by the bcr capture probe indicates the presence of the Philadelphia translocation in the sample.

Diagnosis of CML and ALL using the methods of the invention can also be carried out using multiple capture probes that recognize different sequences in the bcr gene. These probes can be used to distinguish translocations containing different breakpoints on chromosome 22. This method is illustrated as follows.

Synthetic Oligonucleotides as Model Targets, Capture Probes, and Detector Probes Model Targets Two model targets were designed to mimic ALL and CML chimeric mRNAs. The ALL model target (40 mer) contains 20 nucleotides of bcr sequence (nucleotides 1594–1613) and 20 nucleotides of abl sequence (nucleotides 463–482).

ALL Model Target:

bcr region     ‖     abl region
5' gctccaatgagaacctcaccTAGCATCTGACTTTGAGCCT 3'

(SEQ ID NO:1)

The CML model target (40 mer) contains 20 nucleotides of CML-specific bcr sequence (nucleotides 3349–3368) and 20 nucleotides of the same abl sequence as the ALL model target (nucleotides 463–482).

CML Model Target:

bcr region     ‖     abl region
5' actcagccactggatttaagTAGCATCTGACTTTGAGCCT 3'

(SEQ ID NO:2)

Capture Probes

The ALL capture probe, which is an 18 mer, 5'-carboxylated, and complementary to bcr region of the ALL target, has the following sequence.

ALL Capture Probe:

5' HOOC-tgaggttctcattggagc 3' (SEQ ID NO:3)

The CML capture probe, which is an 18 mer, 5'-carboxylated, and complementary to the bcr region of the CML target probe, has the following sequence.

CML Capture Probe:

5' HOOC-taaatccagtggctgagt 3' (SEQ ID NO:4)

Two imperfectly complementary (2 and 4 mismatches) CML capture probes were made to examine the specificity of hybridization. Probe 2MS, which contains 2 mismatches (underlined), has the following sequence.

Probe 2MS:

5' HOOC-taaatGcagtgCctgagt 3' (SEQ ID NO:5)

Probe 4MS, which contains 4 mismatches, has the following sequence.

Probe 4MS:

5' HOOC-taTatGcagtgCctCagt 3' (SEQ ID NO:6)

Detector Probe

The detector probe (DP, 20 mer), which is labeled with FITC, is complementary to the abl sequence common to both the ALL and CML model targets. The detector probe has the following sequence.

Detector Probe (DP):

5' FITC-AGGCTCAAAGTCAGATGCTA-FITC 3' (SEQ ID NO:7)

Manufacture of a Device for Detecting and Distinguishing Philadelphia Translocations A coupling reaction employing 1-Ethyl-3-(3-Dimethyl-Aminopropyl) Carbodiimide (EDAC) was used to attach capture probes to Affi-Gel 102 beads for use as binding elements as follows.

An Affi-Gel 102 gel slurry (0.5 ml) was mixed with 500 nmole of DNA oligomer (either ALL or CML-specific capture probe) in 0.5 ml water and the pH was adjusted to 4.8–5.0 with 50µl 0.2N HCl. After addition of 0.5 mg EDAC, the pH was adjusted again with 30 µl 0.2N HCl to a pH of 5.0, and the mixture was shaken for 3 hours at room temperature. A coupling efficiency of 70% was reached, binding 350 nmole of DNA oligomer to 400 µl of moist gel beads. A glass capillary with an inner diameter of approximately 2.5 mm was plugged at one end with glass wool and then loaded with alternating layers of gel beads with or without attached capture probes.

Demonstration of Multiple Target Capture on the Device

Synthetic model targets (ALL or CML) were mixed with detector probe in 3×SSC(1×SSC=150 mM NaCl, 15 mM sodium citrate) so that all probes were at a concentration of 1 µM. After heating to 70° C. for 5 minutes, model targets and detector probes were hybridized at room temperature for 1 hour. Aliquots of this mixture were diluted with 3×SSC to give a final concentration of 25 pmole hybrid, in a total volume of 300 µl. The ALL target-detector probe hybrid was passed through a capillary containing alternating layers of beads containing either ALL, CML, or no capture probes (see above), with a flow rate of 75 µl/minute. The capillary was then washed twice with 1 ml 3×SSC. The area of the capillary containing the gel-bed was imaged with a CCD device, using an appropriate system for excitation of the FITC fluorophore and capturing the FITC specific fluorescent light.

Figure 4A:
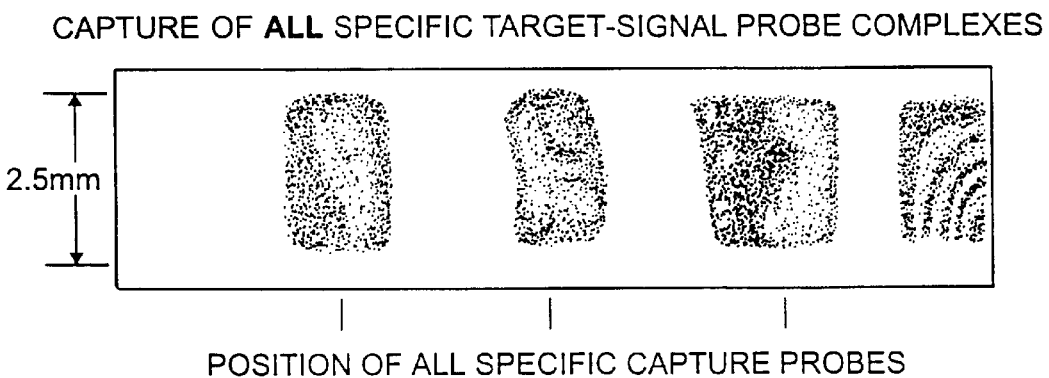
FIG. 4A is an electronic image showing the fluorescence signal of acute lymphocytic leukemia (ALL)-specific target-detector probe complexes captured in a device of the invention.
Figure 4B:
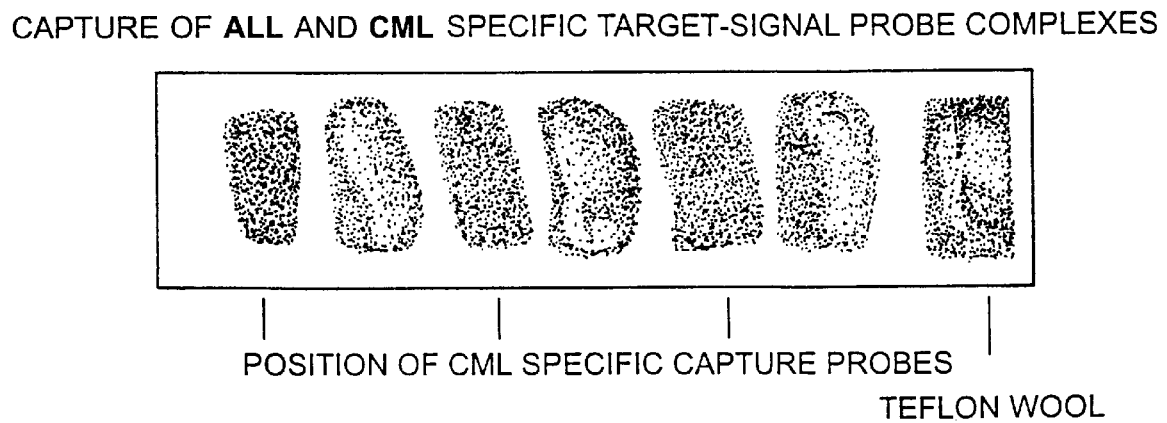
FIG. 4B is an electronic image showing the fluorescence signal of acute lymphocytic leukemia (ALL)-specific and chronic myelogenous leukemia (CML)-specific target-detector probe complexes on a device of the invention.

FIG. 4A shows that all three areas containing ALL-specific capture probes captured some of the model target-detector probe complex. The CML-specific target-detector probe complex was then applied to the capillary under the same conditions, and after washing the capillary free of unbound material, the capillary was imaged again. FIG. 4B shows capture of CML-specific target complexes in gel zones containing CML-specific capture probes. The areas of the gel between the CML and ALL-specific gel beds contained no capture probes, and therefore remain non-fluorescent. The glass wool plug shows some non-specific autofluorescence.

Demonstration of Target Specificity

Figure 5:
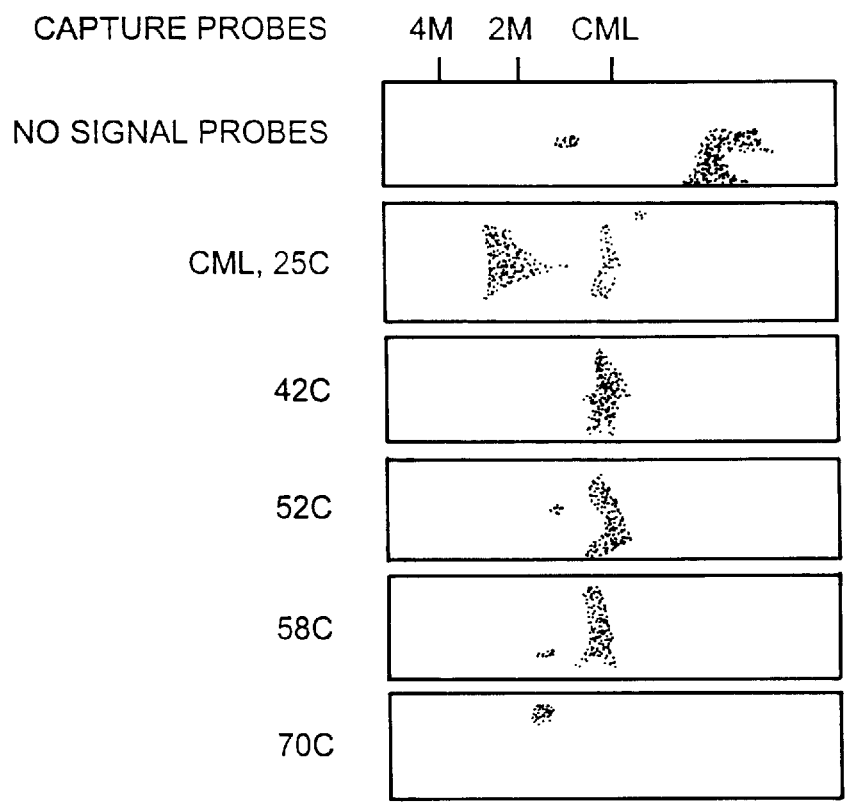
FIG. 5 is a series of computer-generated images showing specificity of CML target capture on a device of the invention.

A glass capillary was loaded with a single layer of CML-specific capture gel, and one layer each of gel containing the 2 mismatch (2MS) or 4 mismatch (4MS) capture probes, spaced by a gel layer without any capture probes. The CML-specific model target-detector probe hybrid (5 pmole in 100 μl) was applied to the capillary at a flow rate of 0.013 ml/minute. The capillary was then washed with 1 ml each of 3×SSC at 25° C., 42° C., 52° C., 58° C., and 70° C. The capillary was imaged before application of target-detector probe complex and after each wash. Different exposure times were chosen for each image to avoid over or underexposure of critical areas. FIG. 5 shows the autofluorescence of the glass wool only (after prolonged exposure), before application of the CML target. Upon application of the CML model target at room temperature (approximately 23° C.), binding occurred to the 2MS mismatch and the CML-specific capture zone, but not the 4MS mismatch zone.

After raising the temperature to 42° C., the model target is released from the 2MS mismatch, but not from the CML model target zone, indicating that target-specific capture in specific zones of the device can be achieved at the appropriate temperature.

Other Embodiments

It is to be understood that, while the invention has been described in conjunction with the detailed description thereof, the foregoing description is intended to illustrate and not limit the scope of the invention. Other aspects, advantages, and modifications of the invention are within the scope of the following claims.

What is claimed is:

1. An assay device for isolating a plurality of different analytes from a sample, said device comprising a tube containing a linear series of porous, cylindrical binding elements, each linked to a distinct binding factor to which a specific component binds, wherein said specific component corresponds to one of said different analytes, and wherein each of said binding elements has a central axis that coincides with a central axis of the tube, and is configured to sealingly contact the interior surface of said tube along the entire circumference of the binding element.

2. The device of claim 1, wherein said distinct binding factor of at least one of said binding elements comprises a capture probe, and said specific component comprises a target analyte.

3. The device of claim 1, wherein said distinct binding factor of at least one of said binding elements comprises a member of a specific binding pair, and said specific component comprises the other member of said specific binding pair and a capture probe that binds to a particular target analyte.

4. The device of claim 1, wherein said tube is a capillary tube.

5. The device of claim 1, wherein said distinct binding factor of at least one of said binding elements comprises a nucleic acid.

6. The device of claim 5, wherein said nucleic acid comprises a portion of an autocatalytically replicable nucleic acid.

7. The device of claim 1, wherein said distinct binding factor of at least one of said binding elements comprises a polypeptide.

8. The device of claim 1, wherein at least two of said binding elements are separated from one another by regions lacking distinct binding factors.

9. A method for detecting the presence of an analyte in a sample, said method comprising the steps of:

labeling said analyte with a detectable label;

contacting said analyte in the sample with a capture probe to form an analyte-capture probe complex immobilized on a specific binding element in the tube of the device of claim 1;

removing from said complex said detectable label that is not specifically bound to said analyte in said complex; and detecting said detectable label in said binding element as a measure of the presence of said analyte in said sample.

10. The method of claim 9, wherein said detectable label is a component of a detector probe.

11. The method of claim 9, wherein said distinct binding factor comprises said capture probe and said contacting step is carried out by passing said sample through said tube, and wherein the analyte is immobilized to a specific binding element via the capture probe.

12. The method of claim 11, wherein said sample is passed through said tube multiple times.

13. The method of claim 11, wherein said sample is mechanically pumped through said tube.

14. The method of claim 9, wherein said analyte is introduced into said tube by application of an electric field to said sample.

15. The method of claim 9, wherein said analyte comprises a nucleic acid, a polypeptide, a carbohydrate, a lipid, a metabolite, or a drug.

16. The method of claim 10, wherein said detector probe comprises a nucleic acid or a polypeptide.

17. The method of claim 9, wherein said capture probe comprises a nucleic acid or a polypeptide.

18. The method of claim 10, wherein said analyte comprises a nucleic acid; said detector probe comprises a portion of an autocatalytically replicable nucleic acid on one end and a first analyte binding element on the other end; said capture probe comprises the remainder of said autocatalytically replicable nucleic acid on one end and a second analyte-binding element on the other end; and said first and second analyte-binding elements bind to adjacent nucleotide segments in said nucleic acid analyte;

said method further comprising the steps of ligating said first and second analyte-binding elements to each other to form a replication template, and replicating said template to generate said detectable signal.

19. The method of claim 9, wherein said distinct binding factor of said binding element comprises a member of a specific binding pair, and said capture probe comprises the other member of said specific binding pair.

20. The method of claim 19, wherein said sample is passed through said tube multiple times.

21. The method of claim 19, wherein said sample is mechanically pumped through said tube.

22. The method of claim 19, wherein said analyte and said capture probe are introduced into said tube by application of an electric field to said analyte and said capture probe.

23. The method of claim 19, wherein said labeling step and said contacting step are carried out simultaneously.

24. The method of claim 19, wherein said contacting step is carried out before said labeling step.

25. An assay system comprising a means for providing active fluid transport in fluid communication with the tube of the device of claim 1.

26. An assay system comprising a fluid transporter in fluid communication with the tube of the device of claim 1.

27. The method of claim 19, wherein said contacting step is carried out by allowing said sample and said capture probe to enter the tube together.

28. An assay device for isolating an analyte from a sample, said device comprising a channel having an interior lumenal surface and containing a linear series of binding elements, each linked to a distinct binding factor to which a corresponding specific component binds, wherein each of said binding elements comprises the lumenal surface of a distinct region of said channel.

29. A device of claim 28, wherein said channel is a tube.

30. A device of claim 28, wherein at least one of said distinct binding factors is bound to at least one of said binding elements by photolithography.

* * * * *